(12) United States Patent
Ferrari et al.

(10) Patent No.: US 6,291,509 B1
(45) Date of Patent: *Sep. 18, 2001

(54) SYNERGISTIC IMMUNOSUPPRESSANT COMPOSITION CONTAINING A 2,2'-BI-1H-PYRROLE COMPOUND

(75) Inventors: Mario Ferrari, Milan; Paola Gnocchi, Stresa; Maria Chiara Fornasiero, Vigevano; Francesco Colotta, Milan; Roberto D'Alessio, Cinisello Balsamo; Anna Maria Isetta, Rho, all of (IT)

(73) Assignee: Pharmacia & Upjohn SpA, Milan (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/068,555
(22) PCT Filed: Sep. 2, 1997
(86) PCT No.: PCT/EP97/04884
§ 371 Date: May 19, 1998
§ 102(e) Date: May 19, 1998
(87) PCT Pub. No.: WO98/11894
PCT Pub. Date: Mar. 26, 1998

(30) Foreign Application Priority Data

Sep. 20, 1996 (GB) .................................................. 9619706

(51) Int. Cl.$^7$ ................................................... A61K 31/40
(52) U.S. Cl. ............................................................ 514/422
(58) Field of Search .............................................. 514/422

(56) References Cited

FOREIGN PATENT DOCUMENTS

WO 95/17381 * 6/1995 (WO) .

OTHER PUBLICATIONS

Alekhin et al., "Effect of prodigiosin and its combination with immunodepressants on the graft versus host reaction in mice!", Nov. 1983, 28(11), P842–845, see abstract.*

Sibiryak, "Effect of prodigiozan and methluracil on adjuvant arthritis in rats" Antibiotiki, 1983, 28/6, 449–452, see abstract, 1983.*

Tsuji et al., "Immunomodulating properties of prodigiosin 25–C, an antibiotic whihc preferentially suppresses induction of cytotoxic T cells", J. Antibiot., 1992, 45/8 (1295–1302)., 1992.*

Stephen E. Hughes Et Al, "New Immunosuppressive Drugs in Organ Transplantation", J. Clin. Pharmacol. 1996:36:1081–1092.

Ferid Murad Et Al, "Drug Interactions", Goodman & Gilman's 7th Edition, p. 1734.

Stephen M. Hatfield Et Al (Abstract) "Rapamycin and FK506 Differentially Inhibit Mast Cell Cytokine Production and Cytokine–Induced Proliferation and Act as Reciprocal Antagonists", J. Pharmacol. Exp. Ther. (1992), 261(3), 970–6.

Barbara E. Bierer Et Al. (Abstract)"Two Distinct Signal Transmission Pathways in T Lymphocytes are Inhibited by Complexes Formed Between an Immunophilin and Either FK 506 or Rapamycin", Proc. Natl. Acad. Sci. U.S.A. (1990), 9231–5.

B.M. Freed Et Al, (Abstract) "A Comparison of the Effect of Cyclosporine and Steroids on Human T Luymphocyte Responses", Transplant. Proc. (1988), 20(2, Suppl. 2), 233–9.

Barry D. Kahan, (Abstract) "Cyclosporin A, FK 506, Rapamycin: The use of a quantitative Analytic Tool to Discriminate Immunosuppressive Drug Interactions", J. Am. Soc. Nephrol. (1992), 2(Suppl. 3), S222–S227.

* cited by examiner

Primary Examiner—Dwayne C. Jones
(74) Attorney, Agent, or Firm—Oblon, Spivak, McClelland, Maier & Neustadt, P.C.

(57) ABSTRACT

A product containing: (a) an immunosuppressant agent (A) and (b) at least one immunosuppressant 2,2'-bi-1H-pyrrole compound (B) having formula (I) wherein $R_1$ is hydrogen, phenyl, $C_1$–$C_{20}$ alkyl or $C_2$–$C_{20}$ alkenyl, wherein the alkyl and alkenyl groups are unsubstituted or substituted by 1 to 3 substituents, which are the same or different, chosen independently from halogen, $C_1$–$C_6$ alkoxy, hydroxy, aryl and aryloxy; $R_2$ is hydrogen, $C_1$–$C_6$ alkyl, cyano, carboxy or ($C_1$–$C_6$ alkoxy)carbonyl; $R_3$ is halogen, hydroxy or $C_1$–$C_{11}$ alkoxy unsubstitued or substituted by phenyl; $R_4$ is hydrogen, $C_1$–$C_6$ alkyl or phenyl; each of $R_5$ and $R_6$, which are the same or different, is independently hydrogen, $C_2$–$C_{20}$ alkanoyl, $C_3$–$C_{20}$ alkenoyl, phenyl, $C_1$–$C_{20}$ alkyl or $C_2$–$C_{20}$ alkenyl; or two of $R_4$, $R_5$ and $R_6$, taken together, form a $C_4$–$C_{12}$ polymethylene chain, which is unsubstituted or substituted by a $C_1$–$C_{12}$ alkyl, by a $C_2$–$C_{12}$ alkenyl or by a $C_1$–$C_{12}$ alkylidene group; or a pharmaceutically acceptable salt thereof; as a combined preparation for simultaneous, separate or sequential use in immunosuppressant therapy, said preparation having a potentiated immunosuppressive activity with respect to products containing either the immunosuppressant agent (A) or the 2,2'-bi-1H-pyrrole immunosuppressive compound (B).

7 Claims, No Drawings

SYNERGISTIC IMMUNOSUPPRESSANT COMPOSITION CONTAINING A 2,2'-BI-1H-PYRROLE COMPOUND

This application is a 371 of PCT/EP97/04884 filed on Sep. 2, 1997.

The present invention relates to a combination preparation containing:

(a) an immunosuppressant agent (A), and
(b) an immunosuppressant 2,2'-bi-1H-pyrrole compound (B), as herein defined.

The preparation has an increased immunosuppressive activity, relative to the sum of the effects produced by immunosuppressant drugs (A) or (B) used alone, allowing greater immunosuppressive activity with reduced toxicity.

BACKGROUND OF THE INVENTION

Presently, the most commonly used agents for preventing and treating rejection phenomena associated with organ and tissue transplantations, graft-versus-host diseases and autoimmune diseases are immunosuppressive drugs, e.g. cyclosporin A (CsA), FK506, azathioprine (AZ), methotrexate (Mtx), rapamycin (R), mycophenolate mofetil (Mac) and glucocorticosteroids (Gluc).

All these drug therapies are limited in effectiveness, in part because the doses needed for effective treatments may increase the patient's susceptibility to infection by a variety of opportunistic invaders and, mainly, because of the side effects caused by its direct toxicity. For instance, despite various successful results, a serious limitation to the wider application of CsA in these indications is the toxicity of this substance. In the first place, its marked nephrotoxicity which in some cases is irreversible has to be mentioned here, but also other phenomena such as hypertension, nausea, diabetes, diarrhoea, tremor, tingling or gingival hypertrophy (Palestine A.R. et al.: Am.J.Med. 77 (1984), 652–656), and lymphomagenesis represent complications to be taken seriously, which usually cannot be avoided even with systematic checking of the serum level. In addition, opportunistic infections have to be considered (Dawson T. et al.: J. Rheumatol. 19 (1992), 997), so that by critical benefit-risk assessment an otherwise advantageous CsA medication in many cases has to be sacrificed. FK506 (Tacrolimus) is a macrolide which exerts largely similar effects as CsA, both with regard to its molecular mode of action and its clinical efficacy (Liu J.: Immunol. Today 14 (1993), 290–295; Schreiber S.L. et al.: Immunol. Today 13 (1992), 136–142); these effects, however, may be found already at doses which are less by the factor 20 to 100 compared to CsA (Peters D.H. et al.: Drugs 46 (1993), 746–794). The same is true for rapamycin (R) which again is a macrolide binding intracellularly to the same immunophilin as FK506, although the following biochemical events are differing somewhat (Morris R.E.: Transplant. Rev. 6 (1992), 39–87).

Accordingly, it would be desirable to have a drug capable of potentiating the action of currently used immunosuppressive agents. Ideally, such a drug would increase the efficacy of such immunosuppressive agents and also decrease deleterious side-effects by allowing administration of lower dosage levels.

After an extensive study on the possibility that the effect of an immunosuppressive agent (A) in the present invention is improved by combining it with a variety of compounds, the present inventor has surprisingly discovered that the effect of an immunosuppressive agent (A) is significantly improved and side-effects can be decreased by co-administering it with at least one 2,2'-bi-1H-pyrrole compound (B), as herein defined.

2,2'-Bi-1H-pyrrole compounds (B), according to the present invention are immunosuppressive agents which are known, e.g., from WO 95/17381. Such description also shows a combined use of an immunosuppressant agent (A) and a 2,2'-bi-1H-pyrrole compound (B), in immunosuppressive therapy. However, WO 95/17381 neither shows, nor suggests, that said combined use cause synergistic increase in effect or decrease side-effects in immunosuppressive therapy. In particular, WO 95/17381 neither shows, nor suggests, that the same therapeutic effect obtainable by the combined use of therapeutically effective amounts of an immunosuppressant agent (A) and a 2,2'-bi-1H-pyrrole compound (B) can be similarly also obtained by co-administration of doses by itself inactive of the same two immunosuppressant agents (A) and (B).

DESCRIPTION OF THE INVENTION

In a first aspect, the present invention provides a product containing: (a) an immunosuppressant agent (A) and (b) at least one immunosuppressant 2,2'-bi-1H-pyrrole compound (B) having the following formula (I)

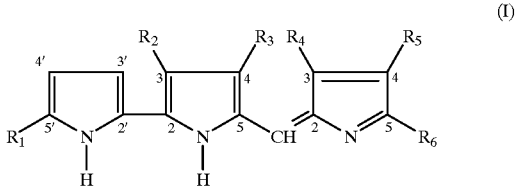

wherein
$R_1$ represents hydrogen, phenyl, $C_1$–$C_{20}$ alkyl or $C_2$–$C_{20}$ alkenyl, wherein the alkyl and alkenyl groups may be unsubstituted or substituted by 1 to 3 substituents chosen independently from halogen, $C_1$–$C_6$ alkoxy, hydroxy, aryl and aryloxy;

$R_2$ represents hydrogen, $C_1$–$C_6$ alkyl, cyano, carboxy or ($C_1$–$C_6$ alkoxy)carbonyl;

$R_3$ represents halogen, hydroxy or $C_1$–$C_{11}$ alkoxy unsubstituted or substituted by phenyl;

$R_4$ represent hydrogen, $C_1$–$C_6$ alkyl or phenyl; each of $R_5$ and $R_6$ independently represents hydrogen, $C_2$–$C_{20}$ alkanoyl, $C_3$–$C_{20}$ alkenoyl, phenyl, $C_1$–$C_{20}$ alkyl or $C_2$–$C_{20}$ alkenyl, wherein the alkanoyl, alkenoyl, alkyl and the alkenyl groups may be unsubstituted or substituted by 1 to 3 substituents chosen independently from halogen, $C_1$–$C_6$ alkoxy, hydroxy, aryl, aryloxy, cyano, carboxy, ($C_1$–$C_6$ alkoxy)carbonyl, ($C_3$–$C_4$ alkenyl)carbamoyl, aralkylcarbamoyl, arylcarbamoyl and —$CONR_cR_d$ in which each of $R_c$ and $R_d$ independently is hydrogen or $C_1$–$C_6$ alkyl or $R_c$ and $R_d$, taken together with the nitrogen atom to which they are linked, form a morpholino or piperidino ring; or two of $R_4$, $R_5$ and $R_6$ taken together form a $C_4$–$C_{12}$ polymethylene chain, which can be unsubstituted or substituted by a $C_1$–$C_{12}$ alkyl, by a $C_2$–$C_{12}$ alkenyl or by a $C_1$–$C_{12}$ alkylidene group, wherein the alkyl, alkenyl and alkylidene groups may be in turn unsubstituted or substituted by a substituent chosen from halogen, $C_1$–$C_6$ alkoxy, hydroxy, cyano, carboxy, ($C_1$–$C_6$ alkoxy)carbonyl, aryloxy and aryl; the remaining one being hydrogen or $C_1$–$C_{12}$ alkyl; or a pharmaceutically acceptable salt thereof; in amounts effective to produce a superadditive immunosuppressant effect, as a combined preparation for simultaneous, separate or sequential use in immunosuppressant therapy. Said preparation having therefore a potentiated immunosuppressive activity with respect to products containing either the immunosuppressive agent (A) or the 2,2'-bi-1H-pyrrole immunosuppressive compound (B).

Also disclosed is a combination preparation containing: (a) an immunosuppressant agent (A) and (b) at least one immunosuppressant 2,2-bi-1H-pyrrole compound (B) of formula (I), as defined above, or a pharmaceutically acceptable salt thereof, in a quantity producing a superadditive immunosuppressive effect.

The present invention also provides a pharmaceutical composition for use in immunosuppressant therapy in mammals, including humans, comprising:
(a) an immunosuppressant agent (A) in a pharmaceutically acceptable carrier and/or excipient, and
(b) at least one immunosuppressive 2,2'-bi-1H-pyrrole compound (B) of formula (I), as defined above, or a pharmaceutically acceptable salt thereof in a pharmaceutically acceptable carrier and/or excipient, in amounts effective to produce a superadditive immunosuppressant effect, said composition having a potentiated immunosuppression activity with respect to a composition containing either the immunosuppressive agent (A) or the 2,2'-bi-1H-pyrrole immunosuppressant compound (B).

A further aspect of the present invention is an immunosuppressant therapy method for use in mammals, including humans, in need thereof, the method comprising administering to said mammal (a) an immunosuppressant agent (A) and (b) at least one immunosuppressant 2,2'-bi-1H-pyrrole compound (B) of formula (I), as defined above, or a pharmaceutically acceptable salt thereof, in amounts effective to produce a superadditive immunosuppressive effect.

The invention also provides a method for lowering the side effects caused by immunosuppressant therapy with an immunosuppressant agent (A) or a 2,2'-bi-1H-pyrrole compound (B) in mammals, including humans, in need thereof, the method comprising administering to said mammal a combination preparation comprising (a) an immunosuppressant agent (A) and (b) at least one 2,2'-bi-1H-pyrrole immunosuppressive compound (B) of formula (I), as defined above, or a pharmaceutically acceptable salt thereof, in a quantity effective to produce a superadditive immunosuppressive effect. Accordingly, said combination preparation can be used for lowering the side effects caused by immunotherapy in mammals, including humans.

In the combined preparations, pharmaceutical compositions and method of treatment according to the present invention only one immunosuppressant 2,2'-bi-1H-pyrrole compound (B), or a pharmaceutically acceptable salt therapy, is preferably used. The combination preparation according to the invention can also include combination packs or compositions in which the constituents are placed side by side and can therefore be administered simultaneously, separately or sequentially to one and the same mammal, including humans.

The immunosuppressant agent (A), which is administered with a 2,2'-bi-1H-pyrrole compound (B), may be for instance one of the following:
(a) cyclosporin A or cyclosporin C, a non-polar cyclic oligopeptide;
(b) FK506, a fungal macrolide immunosuppressant;
(c) azathioprine, or 6 [(1-Methyl-4-nitro-1H-imidazol-5-yl) thio]1H-purine;
(d) methotrexate;
(e) rapamycin, a fungal macrolide immunosuppressant;
(f) mycophenolate mofetil, or 6-(4-hydroxy-6-methoxy-7-methyl- 3-oxo-1,3-dihydroisobenzofuran-5-yl)-4-methyl-4-(E)-hexenoic acid 2-(4-morpholinyl)-ethyl ester; and
(g) an immunosuppressant glucocorticoid, such as prednisone or dexamethasone;
or a mixture of two or more thereof.

Preferably immunosuppressant agent (A) contains at least one of the following: cyclosporin A, azathioprine, prednisone, dexamethasone or mycophenolate mofetil.

More preferably immunosuppressant agent (A) is cyclosporin A. 2,2'-bi-1H-pyrrole compounds (B) of formula (I) as defined above are known from WO 95/17381, J6 1280429 and J0 2250825 and can be obtained as described therein.

The compounds of formula (I) can be represented also by the following tautomeric formula (Ia)

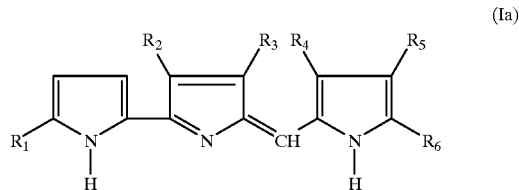

wherein $R_1$, $R_2$, $R_3$, $R_4$, $R_5$ and $R_6$ are as defined above; as described in WO 95/17381.

In a compound of formula (I) the substituents have preferably the following meanings. A halogen atom is preferably chlorine or fluorine. The alkyl, alkoxy, alkenyl, alkanoyl, alkenoyl, alkadienoyl and alkylidene groups may be branched or straight chain groups.

An aryl group as a substituent as well as a moiety in an aryloxy, aralkyl or arylcarbamoyl group is, e.g., an aromatic $C_6$–$C_{20}$ mono- or poly-nuclear moiety, typically phenyl, unsubstituted or substituted by one or two substituents independently chosen from halogen, hydroxy, $C_1$–$C_6$ alkyl and $C_1$–$C_6$ alkoxy.

Accordingly an aralkyl group is e.g. benzyl or phenethyl, in which the phenyl ring is optionally substituted by one or two substituents independently chosen from halogen, hydroxy, $C_1$–$C_6$ alkyl and $C_1$–$C_6$ alkoxy.

A $C_4$–$C_{12}$ polymethylene chain is e.g. a $C_4$–$C_9$ polymethylene chain.

A $C_3$–$C_4$ or $C_3$–$C_6$ alkenyl group is preferably an allyl group.

A $C_1$–$C_6$ alkyl group is preferably a $C_1$–$C_4$ alkyl group, in particular a methyl or ethyl group.

A $C_1$–$C_{12}$ alkyl group is preferably a $C_1$–$C_6$ alkyl group.

An unsubstituted $C_1$–$C_{11}$ alkoxy group is preferably a $C_1$–$C_4$ alkoxy or $C_8$–$C_{11}$ alkoxy group, typically methoxy, ethoxy, propoxy, butoxy and undecyloxy.

A $C_1$–$C_6$ alkoxy group substituted by phenyl is preferably a phenyl-$C_1$–$C_4$ alkoxy group, typically benzyloxy or phenylethoxy.

A $C_1$–$C_{20}$ alkyl group is preferably a $C_5$–$C_{14}$ alkyl group, in particular an undecyl group.

A $C_2$–$C_{20}$ alkenyl group is preferably a $C_5$–$C_{14}$ alkenyl group, in particular an undecenyl group.

A $C_2$–$C_{20}$ alkanoyl group is preferably a $C_5$–$C_{14}$ alkanoyl group, in particular an undecanoyl group.

A $C_3$–$C_{20}$ alkenoyl group is preferably a $C_5$–$C_{14}$ alkenoyl group, in particular an undecenoyl group.

A $C_1$–$C_{12}$ alkylidene group is preferably a $C_1$–$C_8$ alkylidene group, in particular a $C_4$–$C_6$ alkylidene group.

A $C_2$–$C_{12}$ alkenyl group is preferably a $C_3$–$C_6$ alkenyl group.

A ($C_1$–$C_6$ alkoxy)carbonyl group is preferably a ($C_1$–$C_4$ alkoxy)carbonyl group. Examples of pharmaceutically acceptable salts of a compound of formula (I) are either those with inorganic bases, such as sodium, potassium, calcium and aluminium hydroxides, or with organic bases, such as lysine, arginine, N-methyl-glucamine, triethylamine, triethanolamine, dibenzylamine, methylbenzylamine, di-(2-ethyl-hexyl)-amine, piperidine, N-ethylpiperidine, N,N-diethylaminoethylamine, N-ethylmorpholine, β-phenethylamine, N-benzyl-β-phenethylamine, N-benzyl-N,N-dimethylamine and the other acceptable organic amines, as well as the salts with inorganic, e.g. hydrochloric, hydrobromic and sulphuric acids and with organic acids, e.g. citric, tartaric, maleic, malic, fumaric, methanesulphonic and ethanesulphonic acids.

Preferred 2,2'-bi-1H-pyrrole compounds (B) are the compounds of formula (I), wherein $R_1$ is hydrogen or $C_1$–$C_{20}$ alkyl;

$R_2$ and $R_5$ are hydrogen;

$R_3$ represents hydroxy or $C_1$–$C_{11}$ alkoxy unsubstituted or substituted by phenyl;

$R_4$ represents hydrogen or $C_1$–$C_4$ alkyl;

$R_6$ is hydrogen, $C_1$–$C_{14}$ alkyl or $C_2$–$C_{14}$ alkenyl, wherein the alkyl and alkenyl groups may be unsubstituted or substituted by a substituent chosen from halogen, $C_1$–$C_4$ alkoxy, hydroxy, phenyl, phenoxy and cyano;

or $R_5$ and $R_6$, taken together, form a $C_4$–$C_{12}$ polymethylene chain, which can be unsubstituted or substituted by a $C_1$–$C_6$ alkyl, by a $C_3$–$C_6$ alkenyl or by a $C_1$–$C_8$ alkylidene group, wherein the alkyl, alkenyl and alkylidene groups may be in turn unsubstituted or substituted by a substituent chosen from halogen, $C_1$–$C_4$ alkoxy, hydroxy, cyano, phenoxy and phenyl; and the pharmaceutically acceptable salts thereof.

Specific examples of compounds of formula (I) are the following:

4-methoxy-5-{[5-(undec-10-en-1-yl)-2H-pyrrol-2-ylidene]methyl}-2,2'-bi-1H-pyrrole;

4-ethoxy-5-[(5-decyl-2H-pyrrol-2-ylidene)methyl]-2,2'-bi-1H-pyrrole;

4-ethoxy-5-[(5-dodecyl-2H-pyrrol-2-ylidene)methyl]-2,2'-bi-1H-pyrrole;

4-ethoxy-5-[(3,5-nonamethylene-2H-pyrrol-2-ylidene)methyl]-2,2'-bi-1H-pyrrole;

4-ethoxy-5-[(5-undecyl-2H-pyrrol-2-ylidene)methyl]-2,2'-bi-1H-pyrrole; m.p. 94–96° C.*;

4-propoxy-5-[(5-undecyl-2H-pyrrol-2-ylidene)-methyl]-2,2'-bi-1H-pyrrole; m.p. 73–77° C.*;

4-butoxy-5-[(5-undecyl-2H-pyrrol-2-ylidene)methyl]-2,2'-bi-1H-pyrrole; m.p. 81–83° C.*;

4-ethoxy-5-[(5-methyl-2H-pyrrol-2-ylidene)methyl]-2,2'-bi-1H-pyrrole; m.p. 200° (dec)*;

4-methoxy-5-[(5-decyl-2H-pyrrol-2-ylidene)methyl]-2,2'-bi-1H-pyrrole; m.p. 100–116° C.*;

4-methoxy-5-[(5-pentadecyl-2H-pyrrol-2-ylidene)methyl]-2,2'-bi-1H-pyrrole; m.p. 100–104° C.*;

4-methoxy-5-[(5-heptyl-2H-pyrrol-2-ylidene)methyl]-2,2'-bi-1H-pyrrole; m.p. 140–145° C.*;

4-methoxy-5-[(5-phenethyl-2H-pyrrol-2-ylidene)methyl]-2,2'-bi-1H-pyrrole; m.p. 170° C. dec*;

4-methoxy-5-{[5- (5-carboxy-pent-1-yl) -2H-pyrrol-2-ylidene] methyl}-2,2'-bi-1H-pyrrole; m.p. 157–165° C.*;

4-methoxy-5-{[5- (5-carboxy-pent-1-yl) -2H-pyrrol-2-ylidene]methyl}-2,2'-bi-1H-pyrrole methylester; m.p. 138–140° C.*;

4-methoxy-5-[4,5,6,7-tetrahydro-2H-indol-2-ylidene)methyl]-2,2'-bi-1H-pyrrole; m.p. 212° C.*;

4-methoxy-5-[(4-hexyl-4,5,6,7-tetrahydro-2H-indol-2-ylidene)methyl]-2,2'-bi-1H-pyrrole; m.p. 181–184° C.*;

4-ethoxy-5-{[5-(undec-10-en-1-yl)-2H-pyrrol-2-ylidene]methyl}-2,2'-bi-1H-pyrrole; m.p. 80–97° C.*;

4-methoxy-5-[(4-ethyl-3,5-dimethyl-2H-pyrrol-2-ylidene)methyl]-2,2'-bi-1H-pyrrole;

4-methoxy-5-[(4-hexyl-5-methyl-2H-pyrrol-2-ylidene)methyl]-2,2'-bi-1H-pyrrole;

4-methoxy-5-[(5-methyl-4-undecyl-2H-pyrrol-2-ylidene)methyl]-2,2'-bi-1H-pyrrole;

4-methoxy-5-[(5-nonyl-2H-pyrrol-2-ylidene)methyl]-2,2'-bi-1H-pyrrole;

4-methoxy-5-[(5-methyl-4-pentyl-2H-pyrrol-2-ylidene)methyl]-2,2'-bi-1H-pyrrole;

4-isopropoxy-5-[(5-undecyl-2H-pyrrol-2-ylidene)methyl]-2,2'-bi-1H-pyrrole;

4-amyloxy-5-[(5-undecyl-2H-pyrrol-2-ylidene)methyl]-2,2'-bi-1H-pyrrole;

4-undecyloxy-5-[(5-undecyl-2H-pyrrol-2-ylidene)methyl]-2,2'-bi-1H-pyrrole;

4-benzyloxy-5-[(5-undecyl-2H-pyrrol-2-ylidene)methyl]-2,2'-bi-1H-pyrrole; m.p. 90–93° C.*;

4-benzyloxy-5-[(2H-pyrrol-2-ylidene)methyl]-2,2'-bi-1H-pyrrole; m.p. 200–202° C.*;

4-undecyloxy-5-[(2H-pyrrol-2-ylidene)methyl]-2,2'-bi-1H-pyrrole;

4-methoxy-5-[(5-tridecyl-2H-pyrrol-2-ylidene)methyl]-2,2'-bi-1H-pyrrole; m.p. 80–100° C.*;

4-ethoxy-5-[(5-tridecyl-2H-pyrrol-2-ylidene)methyl]-2,2'-bi-1H-pyrrole; m.p. 88–93° C.*;

4-butoxy-5-[(5-tridecyl-2H-pyrrol-2-ylidene)methyl]-2,2'-bi-1H-pyrrole;

4-benzyloxy-5-[(5-tridecyl-2H-pyrrol-2-ylidene)methyl]-2,2'-bi-1H-pyrrole;

4-methoxy-5-[[5-(5-phenoxy-pent-1-yl)-2H-pyrrol-2-ylidene]methyl]-2,2'-bi-1H-pyrrole; m.p. 126–129° C.*;

4-ethoxy-5-[[5-(5-phenoxy-pent-1-yl)-2H-pyrrol-2-ylidene]methyl]-2,2'-bi-1H-pyrrole; m.p. 110–120° C.*;

4-butoxy-5-[[5-(5-phenoxy-pent-1-yl)-2H-pyrrol-2-ylidene]methyl]-2,2'-bi-1H-pyrrole;

4-benzyloxy-5-[[5-(5-phenoxy-pent-1-yl)-2H-pyrrol-2-ylidene]methyl]-2,2'-bi-1H-pyrrole;

4-methoxy-5-[[5-(6-fluoro-hex-1-yl)-2H-pyrrol-2-ylidene]methyl]-2,2'-bi-1H-pyrrole; m.p. 115–124° C.*;

4-methoxy-5-[[5-(6-hydoxy-hex-1-yl)-2H-pyrrol-2-ylidene]methyl]-2,2'-bi-1H-pyrrole; m.p. 118–121° C.*;

4-methoxy-5-[[5-(5-morpholinecarboxamido-pent-1-yl)-2H-pyrrol-2-ylidene]methyl]-2,2'-bi-1H-pyrrole NMR (CDCl$_3$) δppm: 1.2–1.8 (m, 6H); 2.2 (m, 2H); 2.8 (m, 2H); 3.4–3.5 (m, 8H); 4 (s, 3H); 6.2 (m, 2H); 6.8 (m, 1H), 7.1 (s, 1H); 7.4–7.6 (m, 3H); 12.2–12.4 (bs, 1H); 12.5–12.8 (two bs, 2H); * and 4-methoxy-5-[[5-(7-cyano-hept-1-yl)-2H-pyrrol-2-ylidene]methyl]-2,2'-bi-1H-pyrrole NMR (CDCl$_3$) δppm: 1.3–1.8 (m, 10H); 2.3 (m, 2H); 3 (m, 2H); 4.04 (s, 3H); 6.1 (d, 1H); 6.2 (dd, 1H), 6.4 (m, 1H); 6.8 (m, 1H); 6.9 (m, 1H); 7.03 (s, 1H); 7.25 (m, 1H); 12.6–12.7 (two bs, 2H; 12.9 (bs, 1H); *; and the pharmaceutically acceptable salts thereof.

The symbol "*" means determined as hydrochloride.

More preferred 2,2'-bi-1H-pyrrole compounds (B) are the following:

4-ethoxy-5-[(5-undecyl-2H-pyrrol-2-ylidene)methyl]-2,2'-bi-1H-pyrrole;

4-methoxy-5-[(5-tridecyl-2H-pyrrol-2-ylidene)methyl]-2,2'-bi-1H-pyrrole;

4-ethoxy-5-[(5-tridecyl-2H-pyrrol-2-ylidene)methyl]-2,2'-bi-1H-pyrrole;

4-buthoxy-5-[(5-undecyl-2H-pyrrol-2-ylidene)methyl]-2,2'-bi-1H-pyrrole; and 4-benzyloxy-5-[(5-undecyl-2H-pyrrol-2-ylidene)methyl]-2,2'-bi-1H-pyrrole; and the pharmaceutically acceptable salts thereof.

As stated above, co-administration of an immunosuppressant agent (A) and of at least one immunosuppressant 2,2'-bi-1H-pyrrole compound (B), produces a potentiated immunosuppressive activity in synergistic way, thus giving a superadditive immunosuppressive effect, i.e. effect which is grater than the sum of the actions of the individual components.

The superadditive actions of the combination preparations of the present invention are shown for instance by the following tests.

M. Tuberculosis Induced Adjuvant Arthritis in Rats

Adjuvant arthritis is induced in groups of 8 male Lewis rats, weighing 200 g by injecting 100 µg of M. tuberculosis (H37Rv - heat killed) in 50 µl of mineral oil into the plantar surface of the right hind foot pad. The compound 4-benzyloxy-5-[(5-undecyl-2H-pyrrol-2-ylidene)methyl]-2,2'-bi-1H-pyrrole hydrochloride (PNU 156804) is administered at 0.8–0.4–0.2 mg/kg i.v. every other day for a total of 14 administrations, starting on the same day of the mycobacterium injection. CsA is administered at 5 and 1 mg/kg os every day for 28 days, starting on the same day of the mycobacterium injection. When the two compounds are administered in association, the same schedule of administration is used, the doses tested being 0.4 and 0.2 mg/kg i.v. for PNU 156804 and 1 mg/kg os for CsA.

The volumes of the controlateral hind foot pads (systemic, immunologically mediated, disease) are measured pletismographically on days 0 and 28: the differences represent the oedema volumes. The activities of the test compounds are expressed as their capability to inhibit the oedema formation.

The following table summarizes the data obtained in the test.

| Compounds | Dose (mg/kg) | Route | Oedema volume (mm$^3$) | % inhibition |
|---|---|---|---|---|
| PNU 156804 | 0.8 | i.v. | 485 | 66 |
|  | 0.4 | i.v. | 1512 | 0 |
|  | 0.2 | i.v. | 1662 | 0 |
| CsA | 5 | os | 87 | 94 |
|  | 1 | os | 1325 | 6 |
| PNU 156804 + CsA | 0.4 + 1 | i.v. + os | 175 | 88 |
|  | 0.2 + 1 | i.v. + os | 787 | 44 |
| Vehicle | — | i.v. + os | 1408 | — |

These data clearly demonstrate that co-administration of doses by itself inactive of an immunosuppressant agent (A) i.e. cyclosporin A and of a representative immunosuppressant 2,2'-bi-1H-pyrrole compound (B), i.e. PNU 156804, produces a synergic immunosuppressive effect.

Accordingly, the combined preparation of the present invention is an effective new tool in immunosuppressant therapy. In fact it allows administration of lower dosage levels of immunosuppressive agents, thus lowering the side effects caused by commonly used immunosuppressant agents.

The combination preparation of the invention can therefore be used in mammals, including humans, as immunosuppressive agents for the prevention and treatment of rejection phenomena associated with tissue and organ transplantations, graft-versus-host diseases and autoimmune diseases.

Preferred cases of organ and tissue transplants which can be successfully treated by the combination preparation of the invention, hereabove described, are, for example, the cases of heart, kidney and bone marrow transplantation.

Preferred cases of autoimmune diseases which can be successfully treated by the combination preparation of the invention, hereabove described, are for example, the cases of rheumatoid arthritis, systemic lupus erythematosus, juvenile diabetes, autoimmune haemolytic anaemia, miastenia gravis, multiple sclerosis, psoriasis, ulcerative colitis, idiopathic thrombocytopenic purpura, active chronic hepatitis, glomerulonephritis, idiopathic leucopenia, primary biliary cirrhosis, thyroiditis, thyrotoxicosis, dermatomyositis, discoid lupus erythematosus, psoriatic arthritis, regional enteritis, nephrotic syndrome, lupus nephritis, lupoid hepatitis, Sjögren's syndrome, Goodpasture's syndrome, Wegener's granulomatosis, scleroderma, Sezary's disease, uveitis and mumps orchitis. Typically rheumatoid arthritis, systemic lupus erythematosus, juvenile diabetes, miastenia gravis, multiple sclerosis and psoriasis.

Given that both component (A) and component (B) of the combination preparation according to the present invention have immunosuppressant activity, the proportions of immunosuppressant agent (A) and of immunosuppressant 2,2'-bi-1H-pyrrole compound (B) can be in the range of 1:50 to 50:1.

Therefore the dosage of component (A) can vary depending on the concentration of component (B), and vice-versa. However, otherwise subactive doses of either immunosuppressant (A) or (B) or of both are preferably used.

In particular, thanks to the superadditive immunosuppressive effect, the amount of each of agent (A) and compound (B) that is administered is preferably from about 5 to about 85% of the single amount of each component that would be administered when given in the absence of the other component, i.e. of its therapeutically effective amount when given alone, although lower levels of component (A) or component (B) may be administered.

For instance, when component (A) of the combination preparation according to the invention is cyclosporin A, suitable therapy comprises, e.g., i.v. administration of approximately (a) 0.1 to 5 mg/kg, preferably about 0.2 to about 2.5 mg/kg of cyclosporin A and (b) approximately 0.03 to 1.5 mg/kg, preferably about 0.06 mg/kg to about 0.7 mg/kg of the immunosuppressant 2,2'-bi-1H-pyrrole compound (B), e.g., PNU 156804. The dose for oral administration in adult humans is in general at most 1 to 15 mg/kg/day of cyclosporin (a) (component (A)), where a serum level of 100 to 200 ng/ml should not be exceeded, and of 0.3 to 15 mg/kg/day of the 2,2'-bi-1H-pyrrole compound (component B), e.g. PNU 156804.

The dosage to be used is, of course, dependent on various factors such as the organism to be treated (e.g., human or animal, age, weight, general state of health), the severity of the symptoms, the disorder to the accompanying treatment with other pharmaceuticals, or the frequency of the treatment. The dosages are in general administered several times per day and preferably once to three times per day. The amounts of the individual active compounds should be within the range given above, e.g. within the tolerable, efficacious dosage range for the organism to be treated.

The oral route is employed, in general, for all conditions requiring the compounds of the invention. Preference is given to intravenous injection or infusion for the acute treatments. For maintenance regimens the oral or parenteral, e.g. intramuscular or subcutaneous, route is preferred.

The nature of the pharmaceutical preparations and compositions according to the invention, in which components (A) and (B) can be in the same or different pharmaceutical dosage forms, will of course depend upon the desired route of administration and physical and chemical compatibility between the two components.

Compounds, i.e. components, (A) and (B) are herein defined as "the active agents" of the invention.

The compositions may be formulated in the conventional manner with the usual ingredients. For example, the active agents of the invention, may be administered in the form of aqueous or oily solutions or suspensions, tablets, pills, gelatine capsules, syrups, drops or suppositories.

Thus, for oral administration, the pharmaceutical compositions, containing the active agents of this invention, are preferably tablets, pills or gelatine capsules which contain the active substance together with diluents, such as lactose, dextrose, sucrose, mannitol, sorbitol, cellulose; lubricants, for instance silica, talc, stearic acid, magnesium or calcium stearate, and/or polyethylene glycols; or they may also contain binders, such as starches, gelatine, methylcellulose, carboxymethylcellulose, gum-arabic, tragacanth, polyvinylpyrrolidone; disaggregating agents, such as starches, alginic acid, alginates, sodium starch glycolate; effervescing mixture; dyestuffs; sweeteners; wetting agents, such as lecithin, polysorbates, lauryl-sulphates and in general, non-toxic and pharmacologically inactive substances used in pharmaceutical formulations.

Said pharmaceutical preparations may be manufactured in known manner, for example by means of mixing, granulating, tabletting, sugar-coating, or film-coating processes.

The liquid dispersions for oral administration may be e.g. syrups, emulsions and suspensions.

The syrups may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain together with the active agent a pharmaceutically acceptable carrier, e.g. sterile water, olive oil, ethyl oleate, glycols, e.g. propylene glycol, and if desired, a suitable amount of lidocaine hydrochloride.

The solutions for intravenous injections or infusions may contain as carrier, for example, sterile water or preferably they may be in the form of sterile aqueous isotonic solutions.

The suppositories may contain together with the active agent a pharmaceutically acceptable carrier, e.g. cocoa butter, polyethylene glycol, a polyoxyethylene sorbitan fatty acid ester surfactant or lecithin.

The following examples illustrate but do not limit the present invention.

FORMULATION EXAMPLE 1

Injectable Solution

| Component (A): Cyclosporin (A) | 75 mg |
| 94% Ethanol and Cremophor EL ® | 3 ml | to be diluted with saline or 5% dextrose solution before administration.

| Component (B): PNU 156804 | 25 mg |
| 94% Ethanol and Cremophor EL ® | 2 ml | to be diluted with saline or 5 dextrose solution before administration.

The above components (A) and (B) can be placed in separate vials. The vials can be combined for preparing a solution on actual use.

FORMULATION EXAMPLE 2

Capsules, each dosed at 0.5 g and containing 50 mg of the active substance can be prepared.

Composition for 200 capsules:

| | |
|---|---|
| 4-benzyloxy-5-[(5-undecyl-2H-pyrrol-2-ylidene)methyl]-2,2'-bi-1H-pyrrole hydrochloride (PNU 156804) | 10 g |
| Lactose | 80 g |
| Corn starch | 5 g |
| Magnesium stearate | 5 g |

This formulation is encapsulated in two-piece hard gelatin capsules and dosed at 0.5 g for each capsule.

FORMULATION EXAMPLE 3

Cyclosporin A: 100 mg

Soft gelatin capsules containing Cyclosporin A 100 mg dispersed/dissolved in a suitable excipient/carrier can be manufactured according to the common galenic technique.

What is claimed is:

1. A product comprising: (A) cyclosporin A and at least one immunosuppressant 2,2'-bi-1H-pyrrole compound (B) selected from the group consisting of:

4-benzyloxy-5-[(undecyl-2H-pyrrol-2-ylidene)methyl]-2,2'-bi-1H-pyrrole;

4-benzyloxy-5-[(2H-pyrrol-2-ylidene)methyl]-2,2'-bi-1H-pyrrole;

4-benzyloxy-5-[(5-tridecyl-2H-pyrrol-2-ylidene)methyl]-2,2'-bi-1H-pyrrole; and 4-benzyloxy-5-[[5-(5-phenoxy-pent-1-yl)-2H-pyrrol-2-ylidene]methyl]-2,2'-bi-1H-pyrrole.

2. The product according to claim 1, wherein the amount of each of (A) cyclosporin A and compound (B) is from 5 to 85% of its therapeutically effective amount when given alone.

3. A method of immunosuppressant therapy in mammals, in need thereof, comprising administering to said mammal (A) cyclosporin A and at least one immunosuppressant 2,2'-bi-1H-pyrrole compound (B) as defined in claim 1, or a pharmaceutically acceptable salt thereof, in an amount effective to produce a superadditive immunosuppressive effect.

4. The method of claim 3, wherein said mammals are humans.

5. A method for lowering the side effects caused by immunosuppressant therapy in mammals, in need thereof, comprising administering to said mammal a combination preparation comprising (A) cyclosporin A and at least one 2,2'-bi-1H-pyrrol immunosuppresive compound (B) as defined in claim 1, or a pharmaceutically acceptable salt thereof, in a quantity effective to produce a superadditive immunosuppresive effect.

6. The method of claim 5, wherein said mammals are humans.

7. The product according to claim 1, wherein the immunosuppressant compound (B) is 4-benzyloxy-5-[(undecyl-2H-pyrrol-2-ylidene)methyl]-2,2'-bi-1H-pyrrole hydrochloride.

* * * * *